United States Patent
Ebied et al.

(10) Patent No.: US 12,298,213 B2
(45) Date of Patent: May 13, 2025

(54) METHODS FOR EXTRACTING AND ANALYZING COMPOUNDS FROM IMPLANTED AND EXCISED MEDICAL DEVICES

(71) Applicant: PolyAnalytik Inc., London (CA)

(72) Inventors: Amer Ebied, London (CA); Eric D. Landry, London (CA); Peng Xiang, London (CA); Solmaz Karamdoust, London (CA)

(73) Assignee: POLYANALYTIK INC.

( * ) Notice: Subject to any disclaimer, the term of this patent is extended or adjusted under 35 U.S.C. 154(b) by 571 days.

(21) Appl. No.: 17/625,032

(22) PCT Filed: Jun. 26, 2020

(86) PCT No.: PCT/CA2020/050886
§ 371 (c)(1),
(2) Date: Jan. 5, 2022

(87) PCT Pub. No.: WO2021/003558
PCT Pub. Date: Jan. 14, 2021

(65) Prior Publication Data
US 2022/0291096 A1    Sep. 15, 2022

Related U.S. Application Data (60) Provisional application No. 62/870,932, filed on Jul. 5, 2019.

(51) Int. Cl.
G01N 1/40       (2006.01)
B01D 11/02      (2006.01)
G01N 33/483     (2006.01)

(52) U.S. Cl.
CPC ....... *G01N 1/4055* (2013.01); *B01D 11/0288* (2013.01); *G01N 33/4833* (2013.01); *B01D 2221/10* (2013.01); *G01N 2001/4061* (2013.01)

(58) Field of Classification Search
CPC ............ G01N 1/4055; G01N 33/4833; G01N 33/487; G01N 33/49; G01N 2001/4061; B01D 11/0288; B01D 2221/10
See application file for complete search history.

(56) References Cited

U.S. PATENT DOCUMENTS 7,553,505 B2 *   6/2009   Ng .................. A61K 31/353
                                              424/757
10,413,845 B1 *  9/2019   Tegen ............... B01D 11/0288
(Continued)

OTHER PUBLICATIONS

International Search Report issued on Sep. 25, 2020 in respect of corresponding PCT International Patent Application No. PCT/CA2020/050886 filed Jun. 26, 2020.
(Continued)

*Primary Examiner* — Suman K Nath
(74) *Attorney, Agent, or Firm* — Stratford Group Ltd.

(57) ABSTRACT

In general, this invention discloses methods for extracting and analyzing coatings from implanted and excised animal tissue medical devices; wherein the coating comprises at least one biodegradable polymer and at least one or more therapeutic ingredients. The present invention describes optimal conditions for extraction and isolation of biodegradable polymers and therapeutics in medical devices or complex pharmaceutical agent formulations prior and after implanting or injecting into animal tissues. Particularly this work relates to accurate isolation and quantification of ppm amounts of polymer and/or therapeutics without biological interferences. The use of GPC/SEC systems equipped with light scattering detectors enables "absolute" or "true"
(Continued)

molecular weight determination. All of these improvements allow for accurate determination of the degradation profile of the polymer/therapeutic component independent of polymer standards used in conventional GPC/SEC.

5 Claims, 5 Drawing Sheets

(56) References Cited

U.S. PATENT DOCUMENTS

| | | | |
|---|---|---|---|
| 2009/0234146 A1* | 9/2009 | Cooney | B01D 11/0288 210/639 |
| 2009/0292351 A1 | 11/2009 | McClain et al. | |

OTHER PUBLICATIONS

Jackson, John K. et al., "Characterization of perivascular poly (lactic-co-glycolic acid) films containing paclitaxel", International Journal of Pharmaceutics, 2004, vol. 293, No. 1-2, p. 97-109.

GPC Application Notebook. IM Leuschnepark 4, 64347 Griesheim, Tosoh Bioscience GMBH, 2017. Sections 1.03, 1.07, 1.11 to 1.13. Retrieved from <TOSOH Applications Database, https://www.separations.eu.tosohbioscience.com/ebooks/gpc-application-notebook/gpc-applicationnotebook.html>.

Barrera-Rivera et al. Characterization of chain dimensions of poly (i:-caprolactone) diols in THF by size—exclusion chromatography coupled with multi-angle light scattering (SEC-MALS). Journal of Polymer Research, 2015, vol. 22, No. 3, p. 25.

Nuuttila, "Gel permeation chromatography methods in the analysis of lactide-based polymers", University of Jyvasklya, Department of Chemistry, 2018, Abstract; section 6.1. Retrieved from <JYX Digital Repository, https://jyx.jyu.fi/handle/123456789/60101>.

Chung, "Polymethacrylate based hybrids for bone regeneration through controlled polymerisation", Imperial College London, Department of Materials, 2015. Abstract; section 4.3. Retrieved from <Materials PhD Theses, http://hdl.handle.net/10044/1/43933>.

Partial Supplementary EP Search Report dated Jun. 28, 2023 for corresponding EP Application No. 20837379.5.

Leach et al., "Degradation of double-walled polymer microspheres of PLLA and P(CPP:SA) 20:80. II. In vivo degradation", Biomaterials, Elsevier, Amsterdam, NL, vol. 19, No. 21, Nov. 1, 1998, pp. 1981-1988, XP004161473.

Walter et al, "Interstitial Taxol delivered From A Biodegradable Polymer Implant Against Experimental Malignant Glioma", Cancer Research, American Association for Cancer Research, U.S., vol. 54, Apr. 15, 1994, pp. 2207-2212, XP002063920.

Kunou et al., "Biodegradable Scleral Implant for Controlled Intraocular Delivery of Betamethasone Phosphate", Journal of Biomedical Materials Research, Wiley, New York, NY, U.S., vol. 51, No. 4, Jan. 1, 2000, pp. 635-641, XP001205588.

Park et al, "Preparation of Biodegradable and Elastic Poly(?-caprolactone-co-lactide) Copolymers and Evaluation as a Localized and Sustained Drug Delivery Carrier", International Journal of Molecular Sciences, [Online], vol. 18, No. 3, Mar. 21, 2017, p. 671, XP055798757.

Lee et al, "Heparin Coating on 3D Printed Poly (l-lactic acid) Biodegradable Cardiovascular Stent Via Mild Surface Modification Approach for Coronary Artery Implantation", Chemical Engineering Journal, Elsevier, Amsterdam, NL, vol. 378, Jul. 2, 2019, XP085832930.

Ullmann's Encyclopedia of Industrial Chemistry, Liquid-Solid Extraction, vol. 21, Theodor Voeste, Klaus Weber, Brent Hiskey and Gerd Brunner.

Office Action for European Patent Application 20837379.5 dated Mar. 5, 2025.

* cited by examiner

METHODS FOR EXTRACTING AND ANALYZING COMPOUNDS FROM IMPLANTED AND EXCISED MEDICAL DEVICES

FIELD OF THE INVENTION

The present disclosure relates to analytical methods for extracting and analyzing polymeric biomaterials from implantable devices including medical, veterinary and dental devices. In particular, the present disclosure is directed to extracting and analyzing trace amounts of polymeric biomaterials from naïve, implanted and subsequently excised implantable devices.

BACKGROUND

Biomaterials are biocompatible materials having been used in various medical devices that treat, augment, or replace any tissue, organ, or function of the body. A large variety of materials including metals, ceramics, glass, and polymers have been developed as biomaterials. In 2017, the worldwide market of biomaterials was worth US$83.8 billion, and forecasted to increase to nearly US$152 billion by 2021, due to the fast development of versatile polymeric biomaterials in recent years. The demand for polymeric biomaterials will show the fastest compound annual growth rate (CAGR) of 17% between 2017 and 2023 and reach a projected US$10.5 billion.

Polymeric biomaterials can be classified into two main groups: biostable and biodegradable polymeric biomaterials. Different from biostable polymeric biomaterials having stable chemical structure and steady performance in the body, biodegradable polymeric biomaterial can be degraded through cleavage of hydrolytically or enzymatically sensitive bonds, or oxidation in polymer leading to polymer erosion. The detection and characterization of biodegradable polymer in medical device compared to biostable polymers thus are more important and usually challenging.

Since the first development of synthetic poly(glycolic acid) based suture system in the 1960s, synthetic biodegradable polymer, with uniform molecular structure and controllable properties has become the major biomaterials used in medical devices such as scaffolds, implants, pharmaceutical agent delivery vectors and sutures. However, due to the polymer degradation, the detection, quantification, and characterization of the biodegradable polymer in medical devices, especially in implanted and excised medical devices are difficult.

Nowadays, coronary artery disease (CAD) is one of the leading causes of death in the world. It accounted for nearly 900,000 death in US in 2016. Over the past two decades, percutaneous transluminal coronary angioplasty (PTCA) with bare-metal stents (BMS) has been used as a treatment for obstructive CAD. However, high percentage of patients experience arterial narrowing or restenosis resulting in the need for reintervention. In 2003, the first-generation DES consisting of a BMS platform coated with an antiproliferative pharmaceutical agent-polymer film was developed to address the draw backs associated with using BMS and to promote healing of the vessel after opening the blockage. However, durable polymers (DP) used in the first-generation DES was found to be associated with an increased risk of sub-acute and delayed stent thrombosis (ST).

Consequentially, to avoid this complication, the new generation DES utilize biodegradable polymers either as part of the pharmaceutical agent-matrix applied to the stent and/or as a replacement for the metal scaffold. Given the association between polymer presence and ST, the new generation DES have shifted to use of faster resorbing biodegradable polymers to reduce the risk of ST. More recently, a new type of DES with extremely low polymer (less than 50 µg of biodegradable polymer per stent) and pharmaceutical agent (less than 10 µg per stent) amounts has also been developed to optimize anti-restenosis effects and vascular healing and minimize inflammatory response. The new developed DES using low amounts of polymers and pharmaceutical agents has shown to have superior safety and efficacy compared with other stents. However, the extracting and analyzing of the polymers and pharmaceutical agents from implanted and excised medical devices with lower polymer and pharmaceutical agent loading become more difficult.

The analysis of polymers and pharmaceutical agents in the naïve, implanted and excised medical devices are very important and required by regulatory bodies like U.S. Food and Drug Administration (FDA). To characterize the polymers and pharmaceutical agents in medical devices, different characterization techniques including surface characterization, bulk characterization, and chromatographic analysis have been extensively developed. Among them, chromatographic analysis such like gel permeation chromatography (GPC) is the essential separation and analysis technique to determine polymer amount and molecular weight (size).

Although GPC systems equipped with multiple detectors including refractive index (RI) detector, light scattering (LS) detector, viscometer, and UV detector have been successfully developed and used to analyze polymers, it is still challenging to detect and characterize trace amount (less than 50 µg) biodegradable polymeric biomaterials in implantable devices through degradation processed which implanted or injected into animal and human bodies. Accurate assessment of the in vivo and in vitro degradation profile of thin polymer coatings on small devices such as DES requires the development of analytical methods with enough selectivity and sensitivity.

In the following patents, detection of the released polymer/pharmaceutical agent content in addition to the degradation products has been determined using conventional GPC/SEC analysis with a refractive index (RI) detector. The conventional method calculates relative values of molecular weight distribution using a calibration curve of standards having different chemistry and structure. Hence, by using conventional methods, it is very challenging to detect, isolate and characterize trace amount of biodegradable polymeric biomaterials in medical devices or pharmaceutical agent before and after in vivo exposure in different tissues.

US 2009/0292351 A1: discloses a device comprising a stent with at least one layer of a bioabsorbable polymer and at least one layer of an active agent. Quantification of the amount of polymer remaining in the stent at each explant time point and the amount of active agent extracted from the coated stent was analysed by GPC. The GPC system comprised of a refractive index detector coupled to a 50A Hewlet Packard Pl-Gel column. The polymer components were detected by refractive index detection and the peak areas were used to determine the amount of polymer remaining in the stents at the explant time point. Polystyrene standards were used to generate the calibration curve.

U.S. Pat. No. 6,592,899 B2: GPC analysis was performed on a Styragel HR-3 column, or equivalent, calibrated with PEG standards using RI detection and chloroform as the eluent, or on a combination of Phenogel, mixed bed, and 500 A columns calibrated with PEG standards using RI detection and tetrahydrofuran as the eluent for the ABA and BAB triblock copolymers. The reported weight averaged molecular weights determined by GPC for biodegradable polyester oligomers, and particularly PLA/PLGA oligomers were conducted using an identical method with polystyrene Standards.

US 2004/0001872 A1: Molecular weights were determined by GPC and $^1$H-NMR, respectively. The reported lactide/glycolide ratios were calculated from $^1$H-NMR data. GPC analysis was performed on a Styragel HR-3 column, or equivalent, calibrated with PEG Standards using RI detection and chloroform as the eluent, or on a combination of Phenogel, mixed bed, and 500 A columns calibrated with PEG standards using RI detection and tetrahydrofuran as the eluent for the ABA and BAB triblock copolymers.

Advanced detection GPC coupled with RI detector, light-scattering (LS) detectors, UV detector and viscometer allow determination of absolute molecular weight, intrinsic viscosity, hydrodynamic radius, chain conformational and structural parameters. The use of LS detectors renders the calibration curves of polymer standards is not necessary. In this case, the measurement is based on the way in which the sample scatters light but not the retention time at which the molecule elutes compared to polymer standards. This technique is independent of the GPC instrument setup conditions and determines the "absolute" or the "true" molecular mass of the polymer directly. Therefore, it enables a more accurate characterization of trace amounts of polymer and degradation products to assess the performance and safety of implantable devices.

To date, the measurement of molecular weight of the polymer in implantable devices has been calculated based on conventional GPC/SEC analysis and the reported values are relative to polymer standards. However, each polymer has a unique size to weight ratio in a given solvent. Also, the chemistry, structure and composition of the polymer differs from the polymer standards used to construct the conventional calibration curves. For these reasons, the relative molecular weight values are not accurate. Furthermore, the conventional method does not provide details including polymer structure, aggregation, composition, hydrodynamic volume and radius of gyration which can provide valuable insight regarding the safety, clinical outcome and efficacy of a polymer in implantable devices. Advanced detection GPC/SEC is a powerful tool that enables these measurements.

Moreover, all the examples mentioned above, use conventional GPC/SEC method for their molecular weight and degradation analysis. Therefore, the calculated values are relative to standards used for calibration. 'True' or absolute molecular weight and structural information independent of the standard are missing.

Despite all of the above developments in field of polymer analysis, certain challenges remain relating to implanted devices. In particular, the main challenges are the development of a novel methodology using advanced detection SEC/GPC to accurately assess and characterize trace amounts of polymeric biomaterials in implantable devices including medical, veterinary and dental devices before and after implanting or injecting into animal and human bodies.

The content of all documents referred to are hereby incorporated by reference in their entirety for all purposes.

SUMMARY OF THE INVENTION

It is an object of the present invention to provide methods for extracting and analyzing polymeric biomaterials from implanted and excised devices.

In accordance with an aspect of the current invention there are methods provided to extract, detect and analyze trace amounts of biostable or/and biodegradable polymers.

In accordance with a further aspect of the present invention there are provided methods to assess the in vitro and in vivo degradation profiles (polymer mass, polymer absolute and relative molecular weights) of the biodegradable polymer components at different degradation time points.

In accordance with a further aspect of the present invention there is provided a method for the extraction of one or more polymeric biomaterials and/or pharmaceutical agents from an implantable medical device, said method comprising the steps:
  i) excised polymers containing tissue and implantable device are dissolved in one, multiple, or mixture of solvents selected from the group comprising of oxygenated solvents, hydrocarbon solvents, halogenated solvents, organic solvents, aqueous buffers, alkaline solutions, and caustic solutions, thereby producing an extraction solution which is collected;
  ii) the excised polymers can optionally be re-washed with solvents thereby producing one or more extraction solutions of polymer degradants;
  iii) the solvent is removed from the different extracts under a stream of nitrogen gas and/or freeze-dried until dryness and then further dried under vacuum to produce a dried extract;
  iv) the dried extract is dissolved in a suitable mobile phase under gentle stirring for 2 to 24 hours between 25-70° C.; and
  v) the dissolved extract is filtered and introduced into autosampler vials for analysis.

In accordance with an additional aspect of the present invention there is provided a method for determining the degradation profile and concentration of one or more polymers or pharmaceutical agents from an excised previously implanted medical device comprising the following steps:
  i) extracting the one or more biodegradable polymers (or pharmaceutical agents) from a medical device, wherein excised polymer containing tissue and medical device are dissolved in a solvent selected from the group comprising chloroform ($CHCl_3$) or HFIP (1,1,1,3,3,3-hexafluoro-2-propanol), thereby producing an extraction solution which is collected, filtered;
  ii) the excised polymers can optionally be re-washed with the solvent thereby producing one or more washed extraction solutions, each of which are filtered;
  iii) the washed filtered extraction solutions are combined with the filtered extraction solution, producing a combined extract;
  iv) the solvent is removed from the combined extract under a stream of nitrogen gas until dryness and then further dried under vacuum to produce a dried extract;
  v) the dried extract is dissolved in a suitable solvent for further analysis;
  vi) determining baseline data including number-average molecular weight (Mn), and weight-average molecular weight (Mw), and calculating polydispersity index (PDI=Mw/Mn) as a measure of molecular weight distribution of a corresponding naïve non-implanted polymer;
  vii) determining degradation data including number-average molecular weight (Mn), and weight-average molecular weight (Mw), and calculating polydispersity index (PDI=Mw/Mn) as a measure of molecular weight distribution of the polymer at various time points after implantation; and viii) correcting the degradation data using the baseline date to provide an accurate degradation profile of the polymer from the excised previously implanted medical device at various time points.

The foregoing and additional aspects and embodiments of the present disclosure will be apparent to those of ordinary skill in the art in view of the detailed description of various embodiments and/or aspects, which is made with reference to the figures.

While the present disclosure is susceptible to various modifications and alternative forms, specific embodiments or implementations have been shown by way of example in the drawings and will be described in detail herein. It should be understood, however, that the disclosure is not intended to be limited to the particular forms disclosed. Rather, the disclosure is to cover all modifications, equivalents, and alternatives falling within the spirit and scope of an invention as defined by the appended claims.

DETAILED DESCRIPTION

Definitions

"Polymer" as used herein, refers to a series of repeating monomeric units that have been polymerized or cross-linked. Any suitable biodegradable polymer can be used to carry out the present invention. It is possible that the polymers of the invention may also comprise two, three, four or more different polymers. Combinations of polymers can be in varying ratios, to provide coatings with differing properties. Those of skill in the art of polymer chemistry will be familiar with the different properties of polymeric compounds.

"Copolymer" as used herein refers to a polymer being composed of two or more different monomers. A copolymer may also and/or alternatively refer to random, block, graft, alternative, copolymers known to those of skill in the art.

"Biocompatible' as used herein, refers to any material that does not cause injury or death to the animal or induce an adverse reaction in an animal when placed in intimate contact with the animal's tissues. Adverse reactions include for example inflammation, infection, fibrotic tissue formation, cell death, or thrombosis. The terms "biocompatible" and "biocompatibility" when used herein are art-recognized and mean that the referent is neither itself toxic to a host (e.g., an animal or human), nor degrades (if it degrades) at a rate that produces byproducts (e.g., monomeric or oligomeric subunits or other byproducts) at toxic concentrations, causes inflammation or irritation, or induces an immune reaction in the host. It is not necessary that any subject composition have a purity of 100% to be deemed biocompatible. Hence, a subject composition may comprise 99%, 98%, 97%, 96%, 95%, 90% 85%, 80%, 75% or even less of biocompatible agents, e.g., including polymers and other materials and excipients described herein, and still be biocompatible.

The terms "biostable", "bioabsorbable", "biodegradable", "bioerodible" and "bioresorbable" are art-recognized synonyms. These terms are used herein interchangeably. Bioabsorbable polymers typically differ from non-bioabsorbable polymers in that the former may be absorbed (e.g., degraded) during use. In certain embodiments, such use involves in vivo use, such as in vivo therapy, and in other certain embodiments, such use involves in vitro use. In general. degradation attributable to biodegradability involves the degradation of a bioabsorbable polymer into its component subunits, or digestion, e.g., by a biochemical process, of the polymer into smaller, non-polymeric subunits. In certain embodiments, biodegradation may occur by enzymatic mediation, degradation in the presence of water (hydrolysis) and/or other chemical species in the body such as oxygen, or both. The bio-absorbability of a polymer may be shown in-vitro as described herein or by methods known to one of skill in the art. An in-vitro test for bioabsorbability of a polymer does not require living cells or other biologic materials to show bioabsorption properties (e.g. degradation, digestion). Thus, resorbtion, resorption, absorption, absorbtion, erosion may also be used synonymously with the terms "bioabsorbable," "biodegradable." "bioerodible," and "bioresorbable." Mechanisms of degradation of a bioaborbable polymer may include, but are not limited to, bulk degradation, surface erosion, and combinations thereof.

The degradation rate of a biodegradable polymer often depends on a variety of factors, including the chemical identity of the linkage responsible for any degradation, the molecular weight, crystallinity, biostability, and degree of cross-linking of such polymer, the physical characteristics (e.g., shape and size) of the implant, and the mode and location of administration. For example, the greater the molecular weight, the higher the degree of crystallinity, and/or the greater the biostability results in a slower biodegradation profile of any bioabsorbable polymer.

"Biomedical implant' as used herein refers to any implant for insertion into the body of a human or animal subject, including but not limited to coronary implants such as valves, defibrillators, pacemakers and stents (e.g., coronary stents, vascular stents including peripheral stents and graft stents), gastrointestinal, respiratory, and urological systems such as urinary tract stents, urethral/prostatic stents, rectal stent, biliary stent, pancreatic stent, LINX, gastric stimulator, diaphragmatic/phrenic nerve stimulator, neurostimulator, surgical mesh, and penile prosthesis), catheters, ocular or cochlear implants, orthopedic implants such as screws, rods, plates and pins, and cosmetic or contraceptive implants/devices.

"Pharmaceutical agent" as used herein refers to any of a variety of drugs or pharmaceutical compounds that can be used as active agents to prevent or treat a disease (meaning any treatment of a disease in a mammal, including preventing the disease, i.e. causing the clinical symptoms of the disease not to develop; inhibiting the disease, i.e. arresting the development of clinical symptoms; and/or relieving the disease, i.e. causing the regression of clinical symptoms). It is possible that the pharmaceutical agents of the invention may also comprise two or more drugs, pharmaceutical compounds and/or vitamins. Pharmaceutical agents include but are not limited to antirestenotic agents, antiproliferative, anti-inflammatory agents, etc. It can also refer to biochemicals that occur naturally in the body including hormones, enzymes, growth factors, antibodies, etc.

"Excised tissue" as used herein refers to the harvested animal tissues containing the biomedical implants, scaffolds, pharmaceutical agent delivery vectors and other medical devices. The animal is euthanized and during necropsy (i.e. gross examination of the organ and the treated vessels) the soft muscle vessels (e.g. arteries, veins, intestinal and digestive track vessels etc.) and organ tissues (e.g. liver, lungs, kidneys, brain, etc.) are harvested by trained highly qualified personnel. The tissues are flash frozen in liquid nitrogen, shipped on dry ice, and stored at −80° C.

"Simulated physiological condition" as used herein refers to a solution of phosphate buffer with a pH of 7.4 at 37° C. Phosphate buffer is prepared by dissolving 1.652 g of monopotassium phosphate ($KH_2PO_4$) and 14.625 g of sodium phosphate dibasic heptahydrate ($Na_2HPO_4 \cdot 7H_2O$) in a 1000 mL volumetric flask with HPLC grade water. Then the pH of the solution is adjusted to 7.4±0.1 with hydrochloric acid (HCl) or sodium hydroxide (NaOH). The final solution is sterilized by autoclave at 120° C. for 30 min.

"Naïve stent" used herein refers to the unused final stent product without further modification.

"Advanced detection SEC/GPC instrumentation" used here in refers to a GPC system equipped with the following detectors; viscometer, refractive index (RI), light scattering, and a UV/Vis photodiode array detector.

The medical devices may be formed from any suitable material, including but not limited to polymers (including stable or inert polymers, organic polymers, organic-inorganic copolymers, inorganic polymers, biostable and biodegradable polymers), metals, metal alloys, inorganic materials such as silicon, and composites thereof, including layered structures with a core of one material and one or more coatings of a different material.

Polymers like poly (lactide co-glycolic acid) (PLGA) are particularly challenging because the lactic and glycolic acid constituents are endogenous molecules. Although GPC/SEC systems equipped with multiple detectors have been developed and used to analyze degradation profiles of biodegradable polymeric biomaterials, the accurate detection and characterization of trace amounts of them remains challenging.

Subjects into which biomedical devices of the invention may be applied or inserted include both human subjects (including male and female subjects and infant, juvenile, adolescent, geriatric subjects) as well as animal subjects (including but not limited to pig, miniature swine, rabbit, mouse, dog, cat, horse, monkey, etc.) for veterinary purposes and/or medical research.

The present disclosure relates to analytical methods for extracting and analyzing polymeric biomaterials and other active compounds from implantable medical devices. In particular, the present disclosure is directed to extracting and analyzing trace amounts of polymeric and oligomeric biomaterials, monomers and pharmaceutical agents from naïve, degraded, implanted and excised medical devices.

Drug eluting stent (DES) is a prominent example of medical devices containing trace amounts of biodegradable polymers and pharmaceutical agent, and is used herein to demonstrate robust analytical methods for extracting, detecting and analyzing of these compounds. The methods described in this patent could also be applied for analyzing other implantable devices containing biodegradable and/or biostable polymers such as pharmaceutical agent/cell/vaccine delivery vectors, scaffolds, implants, sutures, tissue substitutes, biological coatings, etc.

Numerous disclosures demonstrate polymer-drug release profiles with inaccurate representation of the true molecular weight of the polymer degradants due to the lack of polymer standards of equal chemistry and backbone structure. The methods describe the relative MW characterization of the polymer degradation profiles determined by variations of conventional GPC/SEC calibration curves of polymer standards with different chemistries and structure using a refractive index detector with organic mobile phases.

In one embodiment of this invention, the biodegradable polymer, poly(lactic-co-glycolic acid) (PLGA), oligomers, lactic acids, glycolic acids and rapamycin are extracted and analyzed from naïve, degraded, implanted and excised DES. In one embodiment, the biodegradable poly(lactic acid) (PLLA), oligomer, lactic acids and rapamycin are extracted and analyzed from naïve, degraded, implanted and excised DES. In one embodiment, chitosan is extracted, purified and analyzed from pharmaceutical agent. In one embodiment, polycaprolactone (PCL) and caprolactone copolymers, PCL oligomers, monomers and pharmaceutical agents are extracted, purified and analyzed in pharmaceutical agent. In one embodiment, polyurethane and urethan copolymers, oligomers and pharmaceutical agents are extracted, purified and analyzed from naïve, degraded, implanted and excised DES. In one embodiment, DES degradants in degradation buffer solutions containing polymers, oligomers, monomers and pharmaceutical agents are collected, purified and analyzed. In one embodiment, pharmaceutical agent degradation buffer solutions containing polymers, oligomers, monomers and pharmaceutical agents are collected purified and analyzed.

Accordingly, in one embodiment, there is included a method for the extraction and analysis of polymers, oligomers, monomers and pharmaceutical agents from medical devices, the extraction and analysis comprising the following steps:
 (a) extracting polymers, oligomers, monomers and pharmaceutical agents from naïve, degraded, implanted and excised from medical devices;
 (b) extracting polymers, oligomers, monomers and pharmaceutical agents from degradation buffer solutions;
 (c) analyzing extracted polymers, oligomers, monomers and pharmaceutical agents.

In another embodiment, the extracted compounds including polymers, oligomers, monomers and pharmaceutical agents from naïve medical devices are analyzed by GPC, nuclear magnetic resonance (NMR) and differential scanning calorimetry (DSC). In one embodiment, the raw polymer materials used to manufacture the medical devices are analyzed by GPC, Fourier-transform infrared spectroscopy (FTIR), DSC and NMR. In one embodiment, the chemical structures of polymer coating on DES are analyzed by FTIR and X-ray photoelectron spectroscopy (XPS). In one embodiment, the polymers are isolated from extraction containing polymers, oligomers, monomers and pharmaceutical agents from medical devices, and then analyzed by NMR.

In yet another embodiment, the naïve medical device is washed with saline, ethanol, methanol, or other solvents to remove stabilizer coating prior extraction. In one embodiment, one or more solvents including water, methanol, ethanol, acetone, dichloromethane (DCM), chloroform, tetrahydrofuran (THF), hexane, acetonitrile, toluene, dimethylacetamide (DMAc), dimethylformamide (DMF), dimethyl sulfoxide (DMSO), hexafluoro-2-propanol (HFIP) and ethyl acetate are used to extract polymers, pharmaceutical agents and other compounds need to be analyzed from medical devices. The solvents or solvent combinations selected were based on the polymer, oligomer, monomer and pharmaceutical agent properties. The extraction solvents selected are not degrading, reacting, or modifying the target polymers, pharmaceutical agents and other compounds for analysis. The volume of extraction solvents are varied ranging from 0.5 to 100 mL depending on the size of medical device, the polymer, oligomer, monomer and pharmaceutical agent type and the efficiency of the extraction. The extraction on the same medical device could be repeated up to 10 times.

In a further embodiment, polymers, oligomers, monomers and pharmaceutical agents from extraction solutions are isolated with the flow of nitrogen and dried under vacuum at room temperature or elevated temperature or dried by lyophilization. The drying is not degrading or changing the target polymers, pharmaceutical agents and other compounds for analysis. The dried compounds are further dissolved in selected solvents for different characterization if necessary. One or more analytical techniques including GPC, NMR, FTIR, XPS, XRD, microscopes, DSC, thermogravimetric (TGA). HPLC, GC, MS and FLD are used to characterize dried compounds.

In yet a further embodiment, in vitro degradation buffer solutions of medical devices containing polymers, oligomers, monomers and pharmaceutical agents are collected, purified and analyzed by GPC, NMR, HPLC, GC, mass spectrometry (MS) and fluorescence detector (FLD). In one embodiment, the in vitro degradation buffer solutions are directly injected for HPLC, GC, MS and FLD analysis. In another embodiment, in vitro degradation buffer solutions are dried by lyophilization first and the extracted compounds are re-dissolved in selected solvents for analysis by GPC and NMR. In another embodiment, the dried extract compounds are directly analyzed by DSC, FTIR, TGA and XPS.

In another embodiment, the coronary artery tissue surrounding the DES was sliced into fine pieces. Each sample, containing coronary artery tissue and stents, was submerged in 0.5-10 mL of one, multiple, or mixture of the following solvents including water, methanol, ethanol, acetone, dichloromethane, chloroform, THF, hexane, acetonitrile, toluene, DMAc, DMF, DMSO, HFIP and ethyl acetate. Compounds including polymers, oligomers, monomers and pharmaceutical agents are extracted by the solvents or solvent combinations. The extraction solvents selected are not degrading, reacting, or modifying the target polymers, oligomers, monomers, pharmaceutical agents and other compounds for analysis. The extraction solvents selected do not extract other unwanted animal tissues including proteins, lipids, nucleic acids or interfere with the analysis of target polymers, oligomers, monomers, pharmaceutical agents and other compounds. The extraction is repeated up to 10 times depending on the size of medical device, the tissue, polymer, oligomer, monomer and pharmaceutical agent amount and type, and the efficiency of the extraction. All extraction solutions from same sample are collected, combined and filtered. Polymers, oligomers, monomers and pharmaceutical agents from extraction solutions are isolated with the flow of nitrogen and dried under vacuum at room temperature or elevated temperature or dried by lyophilization. The drying is not degrading or changing the target polymers, pharmaceutical agents and other compounds for analysis. The dried compounds are further dissolved in selected solvents for different characterization if necessary. One or more analytical techniques including GPC, NMR, FTIR, XPS, XRD, microscopes, DSC, thermogravimetric (TGA). HPLC, GC, MS and FLD are used to characterize extracted compounds.

In one further embodiment, GPC characterization is used to determine the mass, molecular weights and chain topology of extracted polymers, oligomers and pharmaceutical agents from the medical device. The GPC analytical conditions including GPC instrument model, detectors, separation columns, mobile phase, calibration type, calibration standard type, concentration of standards, flow rate, analysis temperature, injection volume, etc. are optimized for each medical device. GPC systems are selected from Tosoh, Waters, Malvern, Agilent, etc. depending on the required detectors and detector sensitivity. The GPC mobile phase is using aqueous or organic solvents with additive salts (e.g., $NaNO_3$, NaCl, LiCl, $CF_3COOK$, etc.) and ionic liquids.

In some embodiments, mobile phase including THF, chloroform, dichloromethane, toluene, hexane and HFIP are used for biodegradable polyesters, poly(ester amide)s. In some embodiments, DMAc, DMF, and DMSO are used for biodegradable polyurethanes. In some embodiments, aqueous and acetonitrile are used for water-soluble biodegradable polymers such as chitosan, starch, hyaluronic acid, and polysaccharides.

In some embodiments, size exclusion chromatography (SEC)/GPC columns including organic, aqueous and aqueous/organic compatible columns are used. Separation columns are silica- or polymer-based SEC columns selected from Tosoh, Shodex, Malvern, GE, etc. Calibration standards including polystyrene (PS), poly(methyl methacrylate) (PMMA), poly(ethylene oxide) (PEO), pullulan, etc. are used to calibrate the GPC system. The standard concentrations are ranging from 0.002 to 10 mg/mL depending on the sensitivity of the GPC system and the SEC columns.

In some embodiments, the lower limit of detection (LLOD) and the lower limit of qualification (LLOQ) are determine by Equation 1 and Equation 2, respectively. The Equations are based on the "ICH harmonized tripartite guideline validation of analytical procedures: text and methodology Q2(R1)".

$$LLOD = \frac{3.3\,\sigma}{S} \quad \text{Equation 1}$$

$$LLOQ = \frac{10\,\sigma}{S} \quad \text{Equation 2}$$

where σ=the standard deviation of the response; S=the slope of the calibration curve.

In one embodiment, extracted polymers, oligomers and pharmaceutical agents in the naïve, degraded, implanted and excised medical devices, and degradation buffer are characterized by SEC/GPC. Extracted polymers, oligomers, and pharmaceutical agents amounts and molecular weights (number-average molecular weight, Mn; weight-average molecular weight, Mw and polydispersity) are calculated. Two SEC/GPC calibration methods including GPC-LS equipped with refractive index (RI), ultraviolet (UV), light scattering detectors and viscometer, and conventional GPC (GPC-CC) equipped with only RI and UV detectors are used. The GPC-LS method is used to calculate the absolute molecular weights ($Mn_{LS}$ and $Mw_{LS}$), while the GPC-CC is used to calculate the relative molecular weights ($Mn_{cc}$ and Mw$_{cc}$) using a calibration curve of PS, PMMA, PEO, or pullulan standards. In one embodiment, the GPC-CC analysis is used to calculate molecular weights for polymers, oligomers and pharmaceutical agents having low amounts and low molecular weights.

In one embodiment, GPC-LS measurements are dependent on the optical properties of polymers, oligomers and pharmaceutical agents in the mobile phase used in the analysis. Polymer, oligomer and pharmaceutical agent have a specific optical constant K which is dependent on the squared value of the refractive index increment (dn/dc)$^2$ in each solvent. Measuring absolute molecular weight of polymer, oligomer and pharmaceutical agent by GPC-LS requires an accurate dn/dc for this material. The dn/dc value of each polymer, oligomer and pharmaceutical agent is determined from the plot of RI detector peak area as function of polymer, oligomer and pharmaceutical agent concentration (slope$_{RI}$) and calculated by Equation 3. Similar to the determination of dn/dc, the dA/dc value is determined from the plot of UV detector peak area as function of polymer concentration (slope$_{UV}$) and calculated by Equation 4.

$$\frac{dn}{dc} = \frac{slope_{RI} \times RI \text{ of solvent}}{RI \text{ calibration factor}} \quad \text{Equation 3}$$

$$\frac{dA}{dc} = \frac{slope_{UV}}{UV \text{ calibration factor}} \quad \text{Equation 3}$$

In some embodiments, polymer, oligomer and pharmaceutical agent concentrations (c$_{Polymer}$, c$_{Oligomer}$ and c$_{pharmaceutical\ agent}$) are calculated from the RI peak area using dn/dc value. In some embodiments, polymer, oligomer and pharmaceutical agent concentrations (c$_{Polymer}$, c$_{Oligomer}$ and c$_{pharmaceutical\ agent}$) are calculated from the UV peak area using dA/dc value. In another embodiments, polymer, oligomer and pharmaceutical agent concentrations are calculated from the calibration curve (RI or UV) of polymer, oligomer and pharmaceutical agent. The mass of extracted polymers, oligomers or pharmaceutical agents (m$_{Polymer}$, m$_{Oligomer}$ or m$_{pharmaceutical\ agent}$) are calculated by multiplying their concentrations (c$_{Polymer}$, c$_{Oligomer}$ or c$_{pharmaceutical\ agent}$) obtained from GPC with the volume of solvent (v) used to dissolve each extracted component (Equation 4). In some embodiments, the percent of mass and molecular weight loss of the degraded polymers in the medical device at different degradation time (i) compared to the polymer in the naïve medical are calculated using Equations 4-6.

$$m_{Polymer, Oligomer\ or\ pharmaceutical\ agent} = (c_{Polymer, Oligomer\ or\ Drug} \times v) \quad \text{Equation 4}$$

$$\% \ m_{Polymer,i} \text{loss} = \left(\frac{(m_{Polymer,naïve} - m_{Polymer,i})}{m_{Polymer,naïve}}\right) \cdot 100 \quad \text{Equation 5}$$

$$\% \ Mn_{Polymer,i} \text{loss} = \left(\frac{(Mn_{Polymer,naïve} - Mn_{Polymer,i})}{Mn_{Polymer,naïve}}\right) \cdot 100 \quad \text{Equation 6}$$

$$\% \ Mw_{Polymer,i} \text{loss} = \left(\frac{(Mw_{Polymer,naïve} - Mw_{Polymer,i})}{Mw_{Polymer,naïve}}\right) \cdot 10 \quad \text{Equation 7}$$

EXAMPLES

The operation of the disclosure is illustrated by the following representative examples.

Example 1—Extraction of Biodegradable Polymers and Pharmaceutical Agents from the Naïve Drug Eluting Stent (DES)

The following is the typical polymers and pharmaceutical agent extraction procedure from the naïve DES. The naïve DES was collected by removing the packing. The stent was then soaked in 5 mL of saline solution 30 seconds with light agitation. The stent was then dried by lyophilization immediately.

The extraction solutions could be combined if necessary and then dried by air/nitrogen flow, vacuum, or lyophilization. Gentle heat could be provided during the drying depending on polymer, pharmaceutical agent, and other compounds types. Heat should not degrade or change the target polymers, pharmaceutical agents, and other compounds for analysis.

After removing the extraction solvents, dried polymers, pharmaceutical agents and other compounds extracted from the stent could be used for analysis with different characterization techniques including nuclear magnetic resonance (NMR), GPC, Fourier-transform infrared spectroscopy (FTIR), X-ray photoelectron spectroscopy (XPS), X-ray powder diffraction (XRD), microscopes, differential scanning calorimetry (DSC), thermogravimetric analysis (TGA), high performance liquid chromatography (HPLC), gas chromatography (GC), etc. Among these techniques, GPC is the essential tool to determine the polymer/pharmaceutical agent mass, polymer molecular weights (size) and polymer chain topology. Other techniques were used to determine the chemical structure, physical properties, monomer content and crystallinity of polymers, pharmaceutical agents and other compounds extracted from the medical device.

Example 2—Extraction of Biodegradable Polymers and/or Pharmaceutical Agents from Excised Medical Devices in Tissues—Drug Eluting Stents (DESs)

In one embodiment, the coronary artery tissue surrounding the stent was sliced into fine pieces. Each sample, containing coronary artery tissue and stents, was submerged in 0.5-10 mL of one, multiple, or mixture of the following solvents including water, methanol, ethanol, acetone, dichloromethane, chloroform, THF, hexane, acetonitrile, toluene, DMAc, DMF, DMSO, HFIP and ethyl acetate. The polymer was left to dissolve. The solvents or solvent combinations selected were based on the target polymer, pharmaceutical agent, tissue, and other compounds types. The extraction solvents selected should not degrade, react, or modify the target polymers, pharmaceutical agents and other compounds for analysis. The extraction solvents selected should not extract other unwanted tissues such as proteins, lipids, nucleic acids, from the sample complex which interference with target polymer, pharmaceutical agents and other compounds. The extraction step could be repeat up to 10 times depending on the size of medical device, the tissue, polymer and pharmaceutical agent type, and the efficiency of the extraction.

All extraction solutions from same sample were collected, combined, filtered and transferred to a new vial. The extraction solvents were then removed under a stream of nitrogen gas/air and dried under vacuum or lyophilization. Heat could be provided during the drying depending on polymer, pharmaceutical agent, and other compounds types. Heat should not degrade or change the target polymers, pharmaceutical agents, and other compounds for analysis. After removing the extraction solvents, dried polymers, pharmaceutical agents and other compounds extracted from the stent could be used for analysis with different characterization techniques.

Example 3—Detection and Characterization of Extracts (Biodegradable/Biostable Polymers, Oligomers, Pharmaceutical Agents and Other Compounds) from Medical Device GPC characterization was used to determine the mass, molecular weights and chain topology of extracted polymers, oligomers, pharmaceutical agents and other compounds from the medical device. The GPC analytical conditions including GPC instrument model, detectors, separation columns, mobile phase, calibration type, calibration standard type, concentration of standards, flow rate, analysis temperature, injection volume, etc. were optimized for each medical device.

A typical GPC instrumentation and conditions are shown in the following table

| | |
|---|---|
| Model | High Performance GPC System (Tosoh EcoSEC) HLC-8320GPC from Tosoh Bioscience LLC |
| Detectors | Refractive Index, Light Scattering, UV at 278 nm and Viscometer |
| GPC Columns | 2 × TSKgel GMH$_{HR}$-M |
| Mobile phase | CHCl$_3$ |
| GPC Column Calibration | Polystyrene Standards includes 800 Da, 1 kDa, 2 kDa, 7 kDa, 24 kDa, 60 kDa, 100 kDa, 200 kDa, 400 kDa, 800 kDa |
| Flow Rate | 0.2-1.0 mL/min |
| Temperature | 35° C. |
| Injection Volume | 5-100 μL |

GPC system could be selected from Tosoh, Waters, Malvern, Agilent, etc. depending on the required detectors and detector sensitivity. The GPC mobile phase include using aqueous or organic solvents, while salts (e.g., NaNO$_3$, NaCl, LiCl, CF$_3$COOK, etc.) and ionic liquids could also be used as additives. The common organic solvents such as THF, chloroform, dichloromethane, toluene, hexane, DMAc, DMF, DMSO and HFIP were used for biodegradable polymers such as polyesters and polyurethanes. Aqueous system could be used for water-soluble biodegradable polymers such as chitosan, starch, hyaluronic acid, and polysaccharides. Size exclusion chromatography (SEC) columns including organic, aqueous and aqueous/organic compatible columns were used. Separation columns could be silica- or polymer-based SEC columns selected from Tosoh, Shodex, Malvern, GE, etc. Calibration standards including PS, poly(methyl methacrylate) (PMMA), poly(ethylene oxide) (PEO), pullulan, etc. were used to calibrate the GPC system. The standard concentrations were ranging from 0.002 to 10 mg/mL depending on the sensitivity of the GPC system and the SEC columns.

The dried sample extracted from medical device was dissolved in 1-4 mL mobile phase of GPC system selected. composed of 0.05 M potassium trifluoroacetate (KTFA) in HFIP. Finally, the HFIP polymer solution was analysis by advanced detection SEC/GPC.

The dried extracts were dissolved in 1-4 mL of mobile phase of GPC system on shaker for 1-24 hours. The solution was subsequently filtered and injected into GPC system along with standards.

Example 4—Detection and Characterization of Polymer, Oligomer, Pharmaceutical Agents, and Other Compounds During Degradation Using GPC/SEC The optical properties of refractive index increments (dn/dc) of different polymers in a range of solvents at different temperatures were determined between 0.1-0.2 mL/g and calculated by equation 5 index increment (dn/dc) value of 0.155 mL/g for the polymer in halogenated organic solvent. The detectors used in the molecular characterization of polymer included: a) RI detector to calculate polymer concentration and b) Right angle light scattering (RALS) detector to calculate "absolute" molecular weight averages including $Mn_{LS}$ and $Mw_{LS}$ and the polydispersity index ($Mw_{LS}/Mn_{LS}$, $PDI_{LS}$). By conventional SEC/GPC analysis, polymer molecular weight parameters were calculated relative to poly(methyl methacrylate) (PMMA) standards. Using the RI detector only, a calibration curve of the retention volume as function of PMMA molecular weight was constructed. PLGA molecular weights ($Mn_{CC}$, $Mw_{CC}$, $PDI_{CC}$) were calculated from the retention volume of the PLGA elution peak relative to the calibration curve. The instrument and detectors were calibrated using PMMA and PLGA calibration standards.

Example 5—Calculation of Lower Limit of Detection (LLOD)

Figure 1:
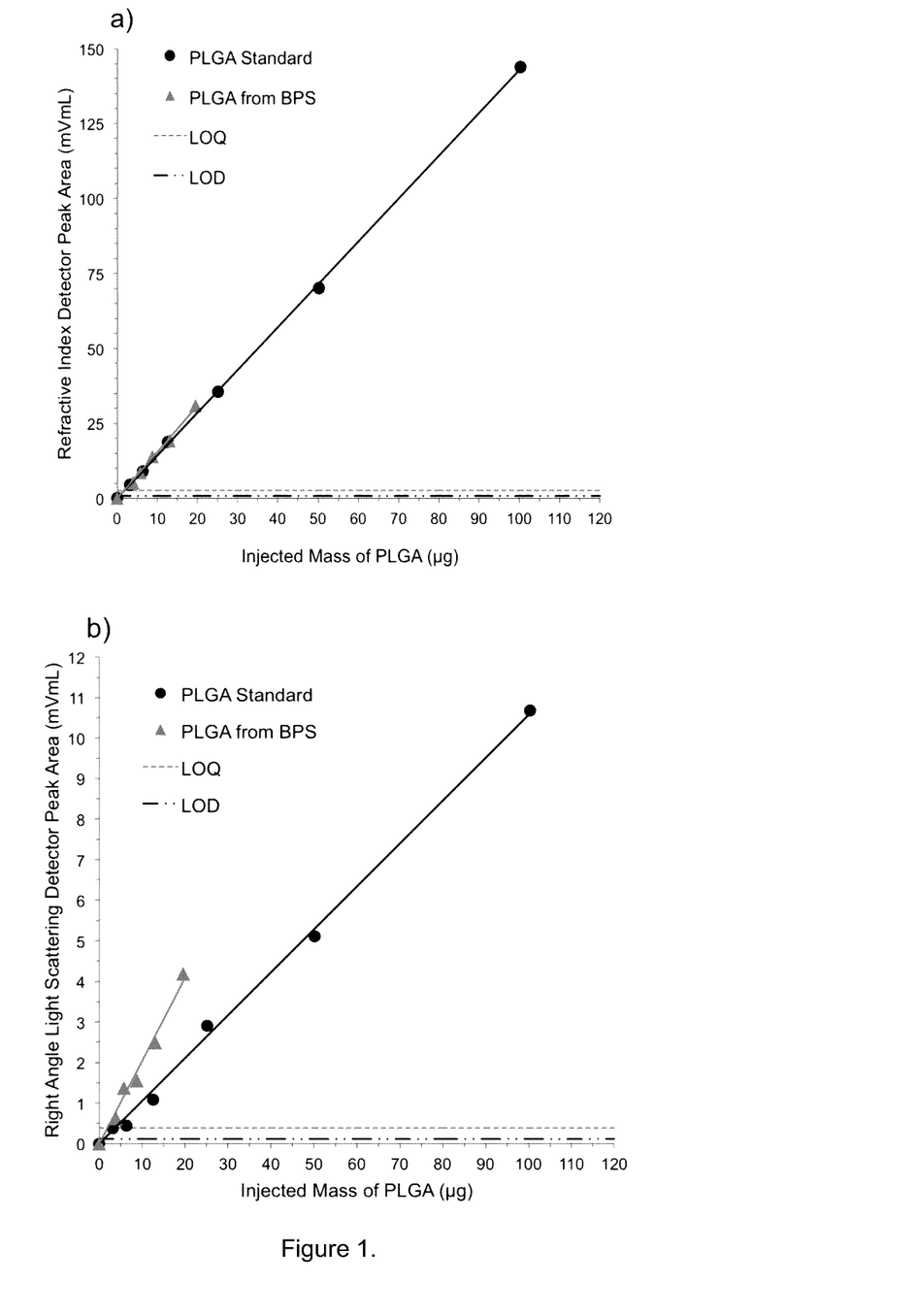
FIGS. 1a and 1b are plots of detector peak area as a function of the various injected masses of serial dilutions of PLGA standard and PLGA from BPS stock solutions analyzed in the lower limit of detection experiment obtained from (a) RI and (b) RALS detectors.

The lower limit of detection (LLOD) of a PLGA standard (50:50, lactide:glycolide) was determined for the advanced detection SEC/GPC instrumentation used in this study. The LLOD results are plotted in FIG. 1 and summarized in Table 2. The targeted mass of PLGA recommended for optimal advanced detection SEC/GPC is 100 μg, although analysis can be carried-out for RI peak areas below 5 mVmL. This set up allows for the detection of trace amounts of polymeric compounds implanted and subsequently excised medical devices.

Example 6—In Vitro Degradation of Biodegradable Polymer and the Release of the Pharmaceutical Agent In vitro degradation of polymer coating from stents in phosphate buffered saline (PBS) at 37° C. was monitored over 16 weeks. The GPC elution profile obtained from the RI detector clearly demonstrated a shift of the polymer peak from 25 mL to later retention volumes at later time points confirming degradation of the polymer and subsequent formation of low molecular weight moieties (FIG. 2—solid line).

Figure 2:
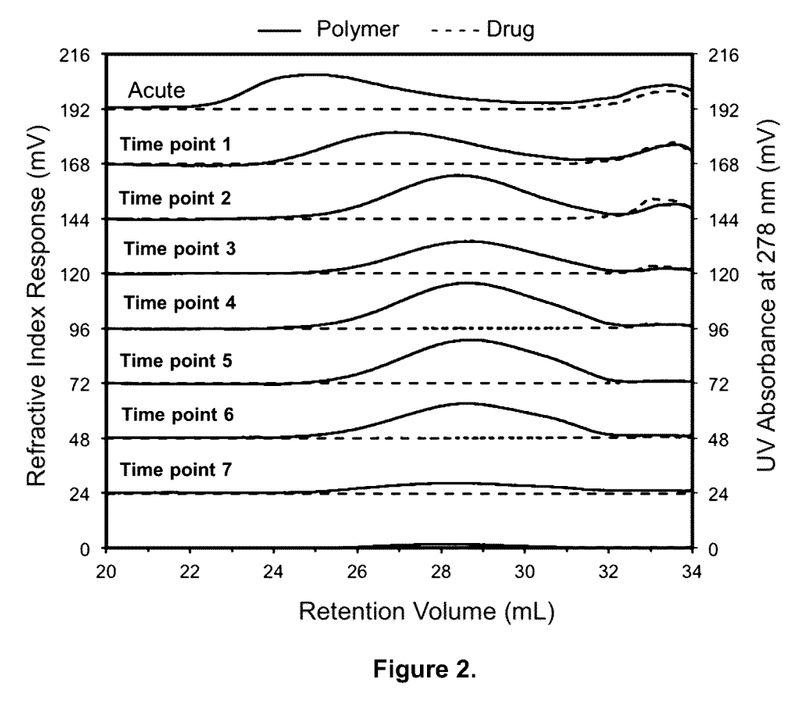
FIG. 2 is an overlay of the GPC elution curves obtained from the RI and UV (dotted line) detector of polymer extracts from the in vitro study at different time points.

Overlays of single injections carried-out for each sample analyzed at the different in vitro time points are shown in FIG. 2. The first peak corresponds to polymer; A lower intensity RI peak also eluted near 33 mL which corresponded to the pharmaceutical agent which was confirmed from the UV absorbance profile monitored at 278 nm (lambda max for sirolimus) (FIG. 2—dashed line).

Figure 3:
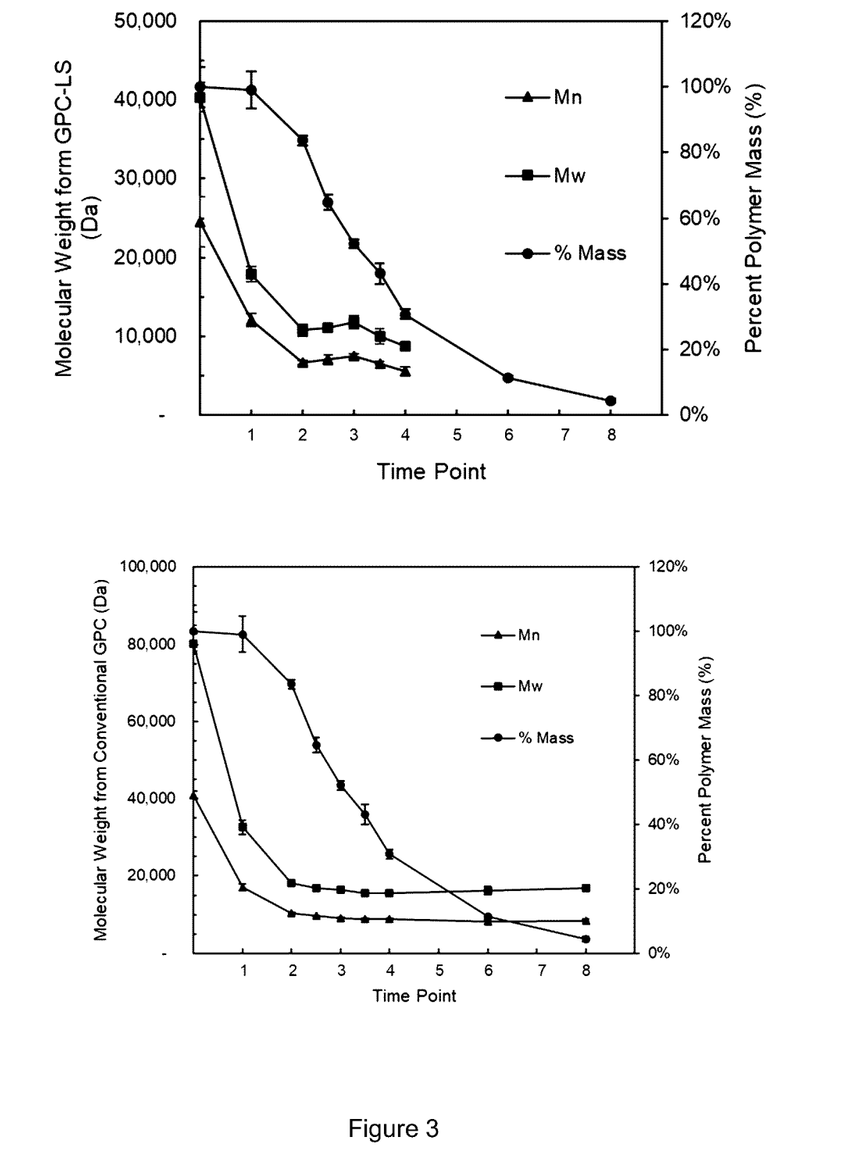
FIG. 3 shows the overlay plots of hydrolytically cleavable polymer molecular weights (Mn and Mw) and percent mass as a function of in vitro degradation time point calculated from (a) GPC-LS and (b) conventional GPC relative to PMMA standards.

The molecular weight profile of the polymer coating at different time points was characterized by GPC-LS to measure absolute molecular weight component and by conventional GPC to measure relative molecular weight moieties relative to PMMA. The conventional GPC results were calculated because the light scattering intensity from which absolute MW was calculated becomes too weak to quantify at later time points due to the reduced concentration and size of the polymer. FIG. 3a-3b. represents the overlay plot of polymer molecular weights including Mn, Mw and percent mass as a function of in vitro degradation time points calculated from light scattering (FIG. 3a) and conventional measurements (FIG. 3b), respectively.

$Mw_{LS}$ of polymer at the baseline time point (i.e. naïve stent) was equal to 40,359±1,895 Da which decreased significantly at week 2 by 55.8±2.8% to 17,840±958 Da and further decreased by 73.2±1.9% at week 4 to 10,807±752 Da. Similarly, the PLGA $Mw_{cc}$ at the baseline was equal to 80,056±2,612 Da which decreased by 59.3±2.3% at week 2 to 32,604±1,880 Da and further decreased by 77.3±0.7% at week 4 to 18,144±580 Da. The mass of polymer coating on the stent at the baseline was equal to 442±27 μg which is within the expected range of polymer mass coating on the stent. The mass of polymer began decreasing at week 4 to 83.6±1.5% (i.e. 370±6 μg) down to 4.3±0.8% (i.e. 19±3 μg) at week 16.

Figure 4:
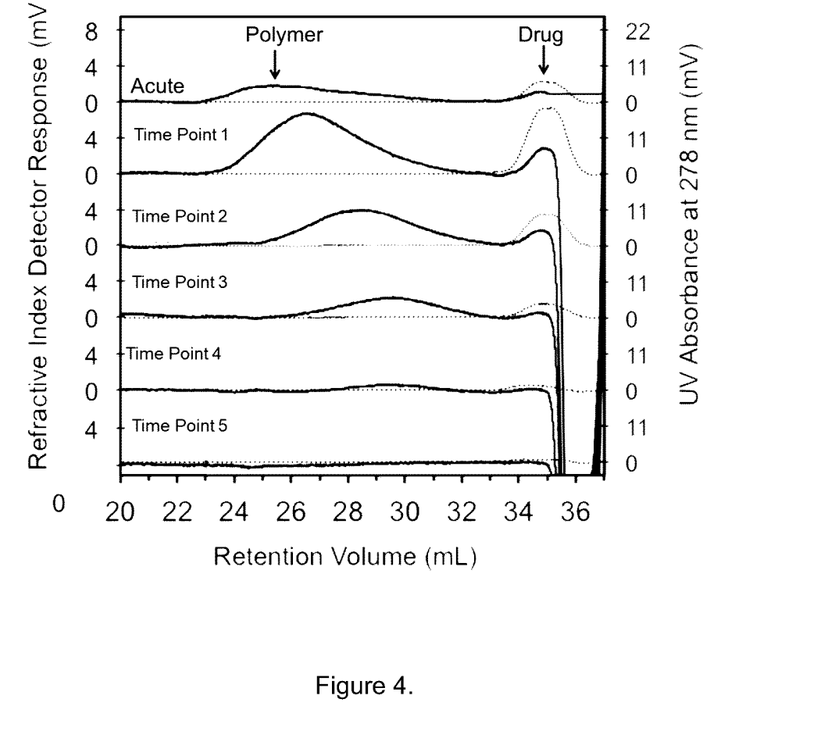
FIG. 4 is an overlay of the GPC elution curves obtained from the RI and UV (dotted line) detector of polymer-pharmaceutical agent extracts from the in vivo study at different time points.
Figure 5:
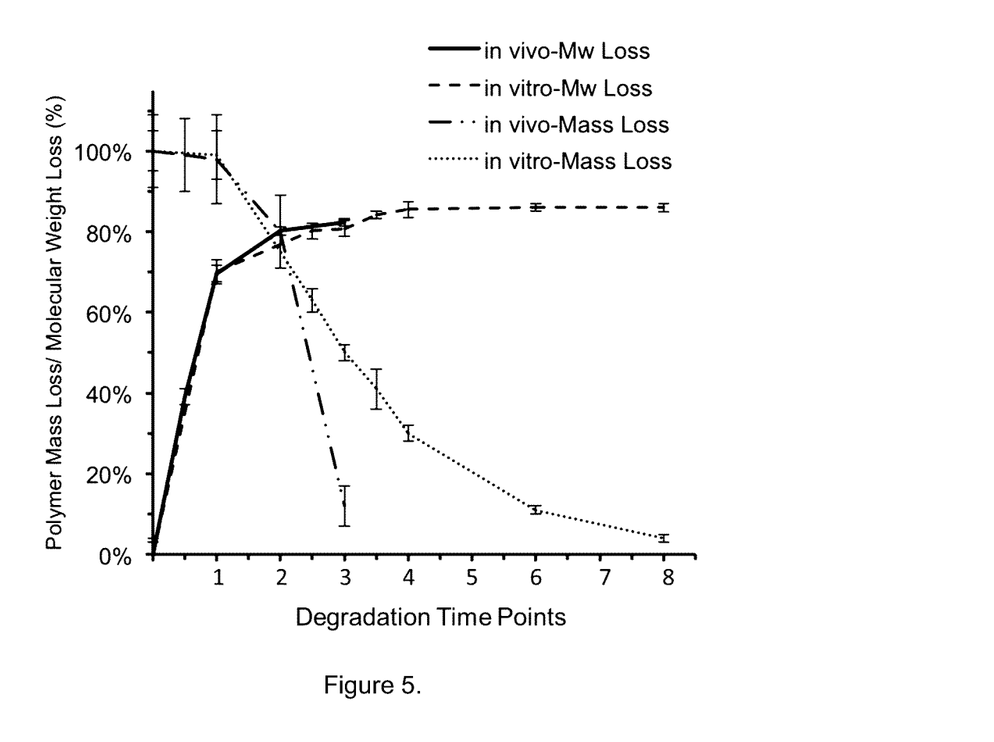
FIG. 5 represents plots of the in vivo and in vitro percent Mw loss and polymer mass measured at different degradation time points.

Example 7—In Vivo Degradation of Biodegradable Polymers and the Release of the Pharmaceutical Agent The polymer extracts at different in vivo degradation time points demonstrated the shifting of the polymer peak to later retention volumes (FIG. 4). The absence of the UV absorbance at 280 nm of the polymer peak confirms that the polymer was quantified and also added the ability to do pharmacokinetic studies on the co-extract pharmaceutical agent in the DES and stented artery samples. The polymer molecular weight (Mw) degradation profiles for the DES incubated in vitro and in vivo were nearly identical whereas the polymer mass loss measured in vivo was much faster compared to in vitro. Interestingly, in both in vitro and in vivo degradation studies the polymer Mw decreased to a maximum of approximately 85% of the initial raw polymer Mw while the mass of the polymer at corresponding time points decreased to below detectable levels. (FIG. 5).

Absolute molecular weight parameters of polymer at the baseline point of the study (i.e. day 0 cohort) were equal to $Mn_{LS}$=31,337±4,340 Da, $Mw_{LS}$=49,180±2,092 Da, and $PDI_{LS}$=1.599±0.225. At the 1 week time point, PLGA molecular weights $Mn_{LS}$ and $Mw_{LS}$ had decreased significantly by 61±4% and 38±3%, respectively. The higher percent loss of $Mn_{LS}$ indicates a higher concentration of shorter polymer chains present at week 1 compared to baseline which suggests that the degradation process at week 1 is targeted mostly at degrading longer polymer chains. This is also demonstrated by the increased $PDI_{LS}$ at week 1 (i.e. 2.475±0.284). There is no measurable mass loss detected at the week 1 time point. Similarly, at week 2, there is also no detected mass loss and $Mn_{LS}$ and $Mw_{LS}$ have decreased by 76±2% and 75±2%, respectively, compared to baseline and the $PDI_{LS}$ decreased to 1.733±0.247. Beyond week 2, SEC/GPC-LS analysis could not be carried-out due to unquantifiable signal detected by the RALS detector (i.e. weeks 3, 4, and 6).

Relative molecular weight parameters of polymer at the baseline point of the study (i.e. day 0 cohort) were equal to $Mn_{CC}$=48,447±6,598 Da, $Mw_{CC}$=94,050±4,778 Da, and $PDI_{CC}$=1.977±0.286. At the 1 week time point, PLGA molecular weights $Mn_{CC}$ and $Mw_{CC}$ had decreased significantly by 52±4% and 47±2%, respectively. For week 1, there was no major difference measured between the percent loss of $Mn_{CC}$ and $Mw_{CC}$ whereas SEC/GPC-LS was able to detect differences between the percent loss of $Mn_{LS}$ and $Mw_{LS}$ due to the LS detection which offered additional insights into the in vivo degradation of polymer. At week 2, $Mn_{CC}$ and $Mw_{CC}$ had decreased by 69±5% and 72±3%, respectively, compared to baseline which follows the same trend as observed with the molecular weight degradation results obtained by SEC/GPC-LS. $PDI_{CC}$ also decreased to 1.791±0.202 at week 2. $Mn_{CC}$ and $Mw_{CC}$ decreased to similar levels at week 3 and 4 by approximately 80% which indicated that the polymer chains detected in week 3 and 4 were similar in molecular weights; however, the mass loss of polymer was increased from 25±9% to 90±2%.

The validated methodology developed to extract polymer from implanted stent in coronary artery tissue was successfully employed to monitor in vivo polymer degradation. The mass of polymer extracted from week 1, and week 2 samples were within the standard deviations of the baseline mass measured at day 0 which was equal to 504±45 μg. Mass loss of polymer was initially detected at week 3 and increased to 90±2% at week 4. No polymer was detected (<52±12 μg) in extracts prepared from 6 test samples pooled together for the week 6 cohort.

Ppm level of polymer extraction and quantification is a critical novelty because some medical devices have less than 50 ug of polymer. Benefit for in vivo study=using less animals, less animal variability, and better accuracy of the polymer degradation kinetics (molecular weight changes and concentration of polymer in tissue). This method improves animal GLP safety studies and provides a valid method to investigate new polymer degradation profiles in vivo for implantable new devices.

While implementations and applications of the present disclosure have been illustrated and described, it is to be understood that the present disclosure is not limited to the precise construction and compositions disclosed herein and that various modifications, changes, and variations can be apparent from the foregoing descriptions without departing from the spirit and scope of an invention as defined in the appended claims.

The invention claimed is:
1. A method for the extraction of one or more polymeric biomaterials and/or pharmaceutical agents from an implantable medical device, said method comprising the steps:
  i) excised polymers containing tissue and implantable device are dissolved in one or more solvents selected from the group comprising of oxygenated solvents, hydrocarbon solvents, halogenated solvents, organic solvents, aqueous buffers, alkaline solutions, and caustic solutions, thereby producing an extraction solution which is collected;
  ii) the excised polymers are re-washed with solvents thereby producing one or more extraction solutions of polymer degradants;
  iii) the solvent is removed from the different extracts under a stream of nitrogen gas and/or freeze-dried until dryness and then further dried under vacuum to produce a dried extract;
  iv) the dried extract is fully dissolved in a mobile phase under gentle stirring for 2 to 24 hours between 25-70° C.; and
  v) the dissolved extract is filtered and introduced into autosampler vials for analysis.

2. The method of claim 1, wherein the medical device is a stent, pharmaceutical agent delivery vehicle, scaffold, or sutures.

3. The method of claim 2, wherein the implanted medical device has been excised from animal organ tissue.

4. The method of claim 1, wherein the mobile phase is selected from the group comprising of oxygenated solvents, hydrocarbon solvents, halogenated solvents, organic solvents, aqueous buffers, alkaline solutions, and caustic solutions.

5. A method for determining a degradation profile and concentration of one or more polymers or pharmaceutical agents from an excised previously implanted medical device comprising the following steps:
   i) extracting one or more biodegradable polymers (or pharmaceutical agents) from a medical device, wherein excised polymer containing tissue and medical device are dissolved in a solvent selected from the group comprising chloroform ($CHCl_3$) or HFIP (1,1,1,3,3,3-hexafluoro-2-propanol), thereby producing an extraction solution which is collected, filtered;
   ii) the excised polymers are re-washed with the solvent thereby producing one or more washed extraction solutions, each of which are filtered;
   iii) the washed filtered extraction solutions are combined with the filtered extraction solution, producing a combined extract;
   iv) the solvent is removed from the combined extract under a stream of nitrogen gas until dryness and then further dried under vacuum to produce a dried extract;
   v) the dried extract is fully dissolved in the solvent for further analysis;
   vi) determining baseline data including number-average molecular weight (Mn), and weight-average molecular weight (Mw), and calculating polydispersity index (PDI-Mw/Mn) as a measure of molecular weight distribution of a corresponding naïve non-implanted polymer;
   vii) determining degradation data including number-average molecular weight (Mn), and weight-average molecular weight (Mw), and calculating polydispersity index (PDI=Mw/Mn) as a measure of molecular weight distribution of the polymer at various time points after implantation; and
   viii) correcting the degradation data using the baseline date to provide an accurate degradation profile of the polymer from the excised previously implanted medical device at various time points.

* * * * *

UNITED STATES PATENT AND TRADEMARK OFFICE
CERTIFICATE OF CORRECTION

PATENT NO. : 12,298,213 B2
APPLICATION NO. : 17/625032
DATED : May 13, 2025
INVENTOR(S) : Amer Ebied et al.

Page 1 of 1

It is certified that error appears in the above-identified patent and that said Letters Patent is hereby corrected as shown below:

In the Claims

Claim 5, Column 18, Line 12 reads:
"(PDI-Mw/Mn) as a measure of molecular weight dis-;"
Whereas it should read:
(PDI=Mw/Mn) as a measure of molecular weight dis-;

Signed and Sealed this
Sixteenth Day of September, 2025

Coke Morgan Stewart
*Acting Director of the United States Patent and Trademark Office*